United States Patent
Moser et al.

(10) Patent No.: US 8,721,615 B2
(45) Date of Patent: May 13, 2014

(54) AMPOULE COMPRISING AN AMPOULE HOLDER

(75) Inventors: Ulrich Moser, Heimiswill (CH); Markus Tschirren, Kirchberg (CH); Annette Drunk, Bern (CH); Jürg Hirschel, Aarau (CH); Celine Kaenel, Zurich (CH); Kevin Mori, Burgdorf (CH); Scott Harris, San Diego, CA (US); John Puddy, San Diego, CA (US); Victor Chang, San Diego, CA (US)

(73) Assignee: TecPharma Licensing AG, Burgdorf (CH)

( * ) Notice: Subject to any disclaimer, the term of this patent is extended or adjusted under 35 U.S.C. 154(b) by 244 days.

(21) Appl. No.: 12/951,772

(22) Filed: Nov. 22, 2010

(65) Prior Publication Data

US 2011/0184373 A1  Jul. 28, 2011

Related U.S. Application Data (63) Continuation of application No. PCT/CH2009/000166, filed on May 19, 2009.

(30) Foreign Application Priority Data

May 24, 2008 (DE) .......... 10 2008 025 011

(51) Int. Cl.
*A61B 19/00* (2006.01)

(52) U.S. Cl.
USPC .......... 604/415; 604/414; 604/416

(58) Field of Classification Search
USPC .......... 604/414, 416, 415
See application file for complete search history.

(56) References Cited

U.S. PATENT DOCUMENTS

| | | | |
|---|---|---|---|
| 3,797,490 A | | 3/1974 | Hurschman et al. |
| 4,968,299 A | * | 11/1990 | Ahlstrand et al. .......... 604/90 |
| 5,435,076 A | * | 7/1995 | Hjertman et al. .......... 34/296 |
| 2007/0102393 A1 | * | 5/2007 | Colin et al. .......... 215/249 |
| 2008/0051729 A1 | * | 2/2008 | Cheng .......... 604/232 |

FOREIGN PATENT DOCUMENTS

WO   WO 2006/090188   8/2006

* cited by examiner

*Primary Examiner* — Leslie Deak
(74) *Attorney, Agent, or Firm* — Dorsey & Whitney LLP; Stuart R. Hemphill, Esq.

(57) ABSTRACT

An ampoule including a casing, a facing side and a seal, wherein the casing has an outer diameter and the seal extends radially beyond the outer diameter and seals the facing side.

12 Claims, 7 Drawing Sheets

AMPOULE COMPRISING AN AMPOULE HOLDER

CROSS-REFERENCED RELATED APPLICATIONS

This application is a continuation of International Patent Application No. PCT/CH2009/000166 filed May 19, 2009, which claims priority to German Patent Application No. 10 2008 025 011.2 filed May 24, 2008, the entire contents of each of which are incorporated herein by reference.

BACKGROUND

The present invention relates to devices for injecting, delivering, administering, infusing or dispensing a substance, and to methods of making and using such devices. Such devices often involve a container, vial, ampoule, carpoule or reservoir for containing the substance, and more particularly, the present invention relates to an ampoule and an ampoule holder for accommodating an ampoule. The term ampoule is intended refer to any suitable container-like item, e.g. a vial, etc., from the field of medical technology, in which is contained a product, e.g. a therapeutic or medicinal substance, to be administered using one of the afore-mentioned devices. The term ampoule can refer to both a one-chamber ampoule and multi-chamber ampoules, e.g. a two-chamber ampoule.

Ampoules are known from the prior art which comprise a cylindrical wall which surrounds a plunger which abuts the inner side of the wall, forming a seal. The plunger can be shifted relative to the wall in the direction of an outlet. The product is situated between the plunger and the outlet. The product container is sealed at the outlet with a seal. The seal can be a so-called septum which can be penetrated by a needle or cannula. The known ampoules comprise an ampoule neck, at which the ampoule tapers, between the cylindrical casing wall and the seal. The known seals have a smaller outer diameter than the cylindrical casing wall. The smaller diameter of the seal serves to enable the ampoule to be inserted into an ampoule holder from the proximal (rear) opening of the ampoule holder and to be pressed into a fixed fit with the ampoule holder via the tapering part of the ampoule neck. The small diameter of the seal enables the septum to be penetrated with a relatively thin needle. Thin needles have the advantage that they do not cause the patient as much pain during injecting, but the disadvantage that the delivering force which has to be applied to the plunger to deliver the product is relatively large, since the product has to be pressed through a thin channel of the needle. This effect is more significant the higher the viscosity of the product contained in the ampoule.

SUMMARY

It is an object of the present invention to provide an ampoule which allows efficient product delivery. It is also an object of the present invention to provide an ampoule holder for holding such an ampoule.

In one embodiment, the present invention comprises an ampoule comprising a casing, a facing side and a seal, wherein the casing has an outer diameter and the seal protrudes or extends radially beyond the outer diameter and seals the facing side.

The present invention relates to product containers, particularly for drugs or therapeutic substances, e.g. a fluid drug, for use in containing and/or administering a drug or therapeutic substance to a patient. The fluid drug can be a homogeneous or heterogeneous fluid. The fluid can be a dispersion, e.g. a suspension or an emulsion. A suspension describes systems consisting of a fluid and particles of a solid, such as particles of powder, suspended in it which are practically insoluble. An emulsion is understood to mean a finely distributed mixture of two different fluids which cannot normally be mixed. Subject product containers will be suitable for storing both low-viscosity and high-viscosity fluid.

In some embodiments of the present invention, the product container can be an ampoule, which also encompasses the terms carpoule, vial, etc. An ampoule is described herein as a representation of product containers.

In some embodiments, an ampoule in accordance with the present invention comprises a casing which is rotationally symmetrical. The casing, i.e. at least a part of it, is cylindrical or tubular. The distal end (front, forward or injection end) of the ampoule comprises a seal which can be embodied such that it can be penetrated by a needle or similar elongated, pointed object. The cylindrical casing, is open at the proximal (rear) end, such that a drive member, e.g. a plunger rod, can act on a plunger or piston which is mounted or carried by the casing.

In some embodiments, one or more plungers can be accommodated in the ampoule. The ampoule can thus be a one-chamber ampoule comprising a single plunger or a multiple-chamber ampoule comprising two plungers which are arranged in succession in the longitudinal direction.

In some embodiments, in a one-chamber ampoule, the fluid product to be administered is between the plunger and the seal. The product can be delivered through the seal by shifting the plunger in the direction of the seal. The plunger, which abuts the inner wall of the casing, forming a seal, can be shifted along the cylindrical part of the casing.

In some embodiments, in a two-chamber ampoule, the drug is first merged or mixed from two constituents, before an injection. The two-chamber ampoule generally comprises a first chamber for a first constituent and a second chamber for a second constituent, wherein in the initial state, the two constituents are separated from each other, for example by a membrane or a plunger. Storing the constituents separately can increase the storage or shelf life of the drug, since the mixed drug only has a relatively short shelf life. The constituents are combined when being mixed. Mixing can be performed by inserting the two-chamber ampoule into a device which is adapted for such ampoules. The first chamber for the first product constituent is arranged between the seal and the first plunger. The second product constituent is arranged between the first plunger and the second plunger. The second plunger is situated proximally with respect to the first plunger. Both plungers abut the inner circumference of the casing, forming a seal, and can be shifted relative to the casing in the longitudinal direction.

In some embodiments, one product constituent, e.g. a solid product constituent such as a particulate or powdery product constituent, can be situated in the first chamber. Storing the product constituent in the first chamber in a dry state can increase the shelf life of the product constituent. A fluid product is situated in the second chamber.

In some embodiments, the two-chamber ampoule can comprise a so-called bypass which comprises a recess, which protrudes radially outwardly, in the cylindrical part of the casing. The recess is formed to be elongated, i.e. longer than it is wide, and exhibits a length which is larger than the length of the first plunger.

In some embodiments, a shifting movement of the second plunger can be transferred onto the first plunger via the product constituent situated in the second chamber. In a shifted position of the first plunger, in which the bypass extends beyond the first plunger both distally and proximally, the second plunger can be moved relative to the first plunger. This can reduce the volume between the first plunger and the second plunger, thus enabling the product constituent contained in the second chamber to flow via the bypass into the distal chamber, i.e. the first chamber, or thus pressing the product constituent contained in the second chamber via the bypass into the distal chamber, i.e. the first chamber. The product constituents thus combined can be mixed. To administer the product mixture, the distal facing side of the second plunger can abut against the proximal facing side of the first plunger. The first plunger and the second plunger can then be jointly moved in the distal direction to deliver the product mixture.

In some embodiments, the seal of the ampoule is formed at its distal (forward) end. The seal can comprise a penetrable means which plastically expands when penetrated, in accordance with the injected object, for example a needle or a continuation of a needle unit. After the body which has penetrated the seal has been removed, the seal can remain open in accordance with the plastic deformation. In some embodiments, the seal comprises a material which can be elastically deformed when penetrated, such that it conforms around the diameter of the penetrating object and abuts it in a fluid seal. When the penetrating object is removed from the seal, the latter can seal itself again in a fluid seal due to its elasticity. The penetration of dirt into the product container and the escape of product from the product container can thus be avoided. If a body is again injected through the seal, the latter can again expand due to its elasticity and again conform against the circumference of the piercing object in a fluid seal. The ampoule can thus also be provided for dispensing product in a number of doses, for each of which a new needle unit is used. A used needle unit can be exchanged for a new one between the injections.

The elastic part of the seal may be referred to as a septum which can, for example, be formed from a synthetic material, from natural rubber or from another suitable material.

In some embodiments, the ampoule exhibits an outer diameter on its cylindrical casing or a portion thereof, wherein the outer diameter can be approximately as large as an inner diameter of an ampoule receptacle, such that the ampoule receptacle can receive and mount (or carry) and/or guide the cylindrical part of the casing.

In accordance with some embodiments of the present invention, the seal protrudes radially beyond the diameter, i.e. the outer circumference area, of the cylindrical part of the ampoule. The diameter which results in the case of a rotationally symmetrical seal can be larger than the diameter of the cylindrical part of the casing. The outer diameter of the seal is the maximum diameter of the ampoule as a whole.

In some embodiments, the seal can comprise at least the septum which exhibits a larger diameter than the cylindrical casing portion and/or protrudes radially beyond the cylindrical casing portion. The seal can also comprise a projection which is formed at the distal end of the casing of the ampoule and protrudes radially beyond the outer circumference of the cylindrical casing part. The projection can be annularly circumferential, such that it can exhibit a larger outer diameter than the cylindrical casing part. The annularly circumferential projection may be referred to as a bulge. The annular projection can be connected, e.g. integrally, to the cylindrical casing portion, directly or indirectly via a portion which exhibits a reduced outer diameter and may be referred to as an ampoule neck. The casing, which is formed from the cylindrical casing part, the annularly circumferential projection and optionally the ampoule neck, can be formed from glass or another suitable material, e.g. a transparent, synthetic material.

In some embodiments, the ampoule neck can exhibit both an outer diameter which is reduced relative to the outer diameter of the seal and the outer diameter of the cylindrical part and/or an inner diameter which is reduced relative to the inner diameter of the cylindrical casing part. The reduced inner diameter means that the plunger can only be shifted as far as the end of the cylindrical part. The length and position of the ampoule holder can be adapted such that the opening and/or the tip of a piercing object inserted through the seal can come to rest axially in the region of the ampoule neck and/or the seal. It is thus possible to avoid the plunger abutting against the piercing object or being pressed too firmly against the piercing object when the piercing object is inserted through the septum into the product container.

In some embodiments, the seal, and also the bulge and the septum, can comprise an approximately cylindrical circumferential area in the region of the seal. The seal can comprise an element which connects the septum and the casing, e.g. the annularly circumferential projection, and/or holds them in a connection. This part can surround the septum and the bulge over their outer circumference. The element can also clasp the septum distally and clasp the bulge proximally to axially secure the septum onto the bulge in a fluid seal. The region exhibiting a reduced diameter of the ampoule neck can be advantageous, since the element can clasp the bulge further radially inwardly than without the region exhibiting a reduced diameter. The element can be a remolded (deformable or deformed) element which during manufacture is correspondingly remolded around the bulge and the septum placed onto the bulge. On the distal facing area of the seal, the element can comprise a breach which is circular and allows direct access to the septum.

In some embodiments, the septum can comprise a disc-shaped region which exhibits approximately the diameter of the bulge. The septum can also comprise a hollow-cylindrical region which projects proximally from the disc-shaped region. The hollow-cylindrical diameter can exhibit an outer diameter which approximately corresponds to the inner diameter of the casing in the axial region of the bulge. The cylindrical region of the septum can thus serve as a centering aid. The inner space or cavity formed by the hollow-cylindrical part of the septum can serve to accommodate one or more openings of the piercing portion of an attached needle unit.

In some embodiments, the bypass of the ampoule can project from the outer circumference of the cylindrical part of the ampoule.

In accordance with the present invention, an ampoule can be arranged together with an ampoule holder, on or in an injection device, wherein the ampoule holder comprises an ampoule receptacle and a fastening member, wherein the radial projection of the seal is arranged, e.g. enclosed, between the ampoule receptacle and the fastening member. This enables the ampoule holder to be axially fixed, i.e. for a movement in the distal (forward) direction and proximal (rearward) direction. An axial clearance of the product container such as may arise can be reduced or even eliminated, as described further below.

In some embodiments, the ampoule receptacle can be sleeve-shaped, with an inner diameter which approximately corresponds to the outer diameter of the cylindrical part of the ampoule, such that the ampoule is laterally guided by the ampoule receptacle. The ampoule receptacle can comprise a thread, e.g. an outer thread, which can engage with a corresponding counter thread of an injection device, such that the ampoule receptacle can be axially shifted into the casing, together with a combined rotational movement. Instead of the thread, an axial guide or other components can also be provided, as long as they allow the axial movement of the ampoule receptacle into the injection device.

In some embodiments, the fastening member can be fastened or fastenable to the ampoule receptacle. The fastening member can be formed integrally with the ampoule receptacle, or, in some embodiments, the ampoule receptacle and the fastening member are separate parts which together form the ampoule holder.

In some embodiments of the present invention, the fastening member can be or comprise a projection which acts on a facing side of the seal of the ampoule, e.g. the distal facing side. The projection can be a resilient member, snapper, cam or the like, wherein the projection can extend radially inwardly from without.

In some embodiments, the ampoule can abut the ampoule receptacle, e.g. the facing side of the ampoule receptacle or a projection on the ampoule receptacle which is directed radially inwardly from an inner circumference, via the proximal side of the seal. In the region where the facing side of the seal is intended to enter into axial abutment, the ampoule receptacle comprises a region exhibiting a reduced inner diameter which is smaller than the outer diameter of the seal and larger than the cylindrical part of the casing. In some embodiments, a facing area of the ampoule receptacle, e.g. the distal end, can provide the abutment for the seal, e.g. its proximal end.

In some preferred embodiments, the ampoule is inserted or able to be inserted with its proximal (rear) end first, i.e. with its cylindrical casing part to the fore, into the ampoule receptacle through the proximal facing side of the ampoule receptacle. When the ampoule is inserted, the fastening member can be deflected and can snap back in the completely inserted position to axially fix the ampoule in at least one direction.

In some preferred embodiments, the fastening member can be connected to the ampoule receptacle in a positive fit such that it is rotationally and axially fixed relative to the ampoule receptacle. The ampoule receptacle and the fastening member can comprise mutually engaging elements which mutually engage or latch into or onto each other, e.g. when the fastening member is placed completely onto the ampoule receptacle.

In some embodiments, wherein a two-chamber ampoule is inserted into the ampoule receptacle instead of a one-chamber ampoule, the ampoule receptacle can comprise a cavity, which extends from the direction of the facing side along the ampoule receptacle, for the bypass of the two-chamber ampoule. A number of such cavities can be provided, distributed over the circumference, such that the ampoule can be inserted into the ampoule receptacle in almost any angular position. The cavity for the bypass can comprise rotational abutments which act in the circumferential direction and prevent a rotation of the ampoule relative to the ampoule receptacle when the ampoule is inserted.

In some embodiments, at least one of the ampoule receptacle and the fastening member can comprise at least one projection, e.g. a cam, which is directed toward the seal. The at least one projection or cam can extend in the longitudinal direction of the ampoule or ampoule holder, e.g. in the distal direction or proximal direction. The facing side of the seal abuts the at least one cam. The point-focussed abutment for the seal which is caused by the cam can reduce a clearance in the axial enclosure of the seal. The at least one projection can be arranged on the ampoule receptacle and/or fastening member rigidly or such that it is sprung or urged or biased, e.g. in the axial direction.

In some embodiments, the at least one projection, e.g. a cam, can be arranged on the ampoule receptacle, namely where the completely inserted product container enters into axial abutment, e.g. on the facing area of the ampoule receptacle. The at least one projection can alternatively or additionally be formed on a projection of the fastening member which is directed radially inwardly, where the fastening member clasps the facing side of the seal.

In some embodiments, the ampoule holder, e.g. the ampoule receptacle and/or the fastening member, can comprise features or structure which enable a needle unit to be fastened to the ampoule holder. The needle unit can be plugged on, e.g. via a conical area, or screwed on, e.g. via a thread. When a needle unit is arranged on the ampoule, it can be fastened to the ampoule holder via a fastening portion. When a needle unit is completely fastened, a piercing object, e.g. a needle, can penetrate the septum and establish a fluid connection between a distal needle tip of the needle unit and the product container. The needle unit is fixedly screwed to the fastening portion which comprises an inner thread with which an outer thread of the needle unit can engage.

In some embodiments, the ampoule receptacle can comprise features or structure, e.g. a thread, using which it can be fastened to an injection device and, when fastened, moved into the injection device by an axial movement, combined with a rotational movement. The ampoule receptacle can comprise one or more latching elements which generate an acoustic and/or tactile signal, for example by latching and/or snapping over a counter element, at selected positions when the ampoule holder is moved into the injection device.

Another advantage of the present invention is that due to the increased diameter of the septum, in some embodiments and preferred embodiments, a thicker continuation or needle can be used for injecting into or penetrating the septum, which with conventional narrow septa is only possible to a restricted extent, i.e. only possible using a thin needle. The thin needle, however, results in an increased delivery resistance. It is therefore preferable for the needle unit to comprise a needle support from which a continuation projects in the proximal direction for penetrating the septum and from which an injection needle projects in the distal direction for injecting into a patient, wherein the continuation exhibits a larger diameter than the injection needle. A fluid channel which transports the product from the product container to the injection needle tip can be contained in the continuation and in the injection needle. The fluid channel can exhibit a larger fluid-guiding cross-section in the region of the continuation than in the region of the injection needle.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

Referring to FIGS. 1-4, a device in accordance with the present invention comprises a needle unit having a number of elements or parts 6, 7, 8, 10 which form a fluid channel which may also be referred to as a fluid-guiding channel. More generally, the parts forming the fluid channel are: a continuation 2, which may also be referred to as a piercing object or means; a needle support 1, which may also be referred to as a cannula support; and an injection needle 3, which may also be referred to as a cannula tube.

The hollow, cylindrical injection needle 3 exhibits a constant outer diameter $D_3$ and a constant inner diameter. At its distal (or forward or front or injection) end, there is a cutting tip which is asymmetrical in the section shown. The injection needle 3 serves for injecting into the skin of a patient and is fastened via its proximal (rear) end to the needle support 1. The fastening shown here consists of a part of the injection needle being accommodated in a hollow-cylindrical bore 5, the inner diameter of which approximately corresponds to the outer diameter of the needle 3. The needle 3 could in principle be pressed or molded in the hollow cylindrical portion of the needle support 1, for example when the needle support 1 is manufactured by injection molding. In some embodiments, the needle is adhered into or on the needle support 1. To prevent stress peaks when transverse forces are exerted on the needle 3, the portion 5 is connected to an expanding region, e.g. a region which expands in the shape of a trumpet, which extends as far as the distal end of the needle support 1, as shown here. Alternatively or additionally, this region can also serve to accommodate adhesive for an adhesive connection between the needle support 1 and the needle 3. The needle 3 may be fastened to the needle support 1 such that it cannot be released. In some embodiments, the needle 3 is made of a metal which is suitable for injection needles, and the needle support 1 is made of plastic.

The needle support 1 comprises a portion 8 of the fluid channel which is connected to the proximal end of the injection needle 3. The portion 8 can be hollow and cylindrical. In some embodiments, the portion 8 exhibits approximately the same fluid-guiding cross-section, e.g. the same inner diameter, as the injection needle 3. This configuration reduces the risk of turbulence or a turbulent flow when fluid transitions or flows from the portion 8 into the portion 10 of the injection needle 3.

The needle support 1 also comprises a portion 7 of the fluid-guiding channel, which exhibits a larger fluid-guiding cross-section than the portions 8 and 10 of the fluid-guiding channel. The portion 7 tapers in the direction of the injection needle 3, i.e. the fluid-guiding cross-section is reduced in the portion 7 in the direction of the needle 3. The fluid-guiding cross-section can be reduced at a constant rate, i.e. a constant gradient, or—as shown here—at an increasing and/or decreasing gradient. In the direction of the injection needle 3, the fluid-guiding cross-section is initially reduced at an increasing gradient. Subsequently, the fluid-guiding cross-section tapers at a decreasing gradient. In a longitudinal section, the portion 7 of the fluid channel can exhibit a concave and/or convex curve of the channel wall. In the direction of the injection needle 3, the wall of the portion initially exhibits a concave curve and subsequently a convex curve. The transitions between the individual portions, for example the transition from concave to convex, can be embodied to be continuous or at least have no sharp edges. The same applies to the transition of the portion 7 into the portion 8.

The needle support comprises a shaft, for example a cylindrical shaft, which extends in the distal direction and in which the needle 3 is arranged and fastened.

The needle support 1 is connected via a join or connection 9 to the continuation 2. The join or connection can be a force-fit, material-fit or positive-fit connection. The join or connection is fluid-proof. A suitable join or connection can be achieved by adhering, pressing, latching or fusing.

The continuation 2 which is connected to the needle support 1 comprises a portion 6 of the fluid-guiding channel. The portion 6 expands in the direction of the injection needle 3, for example in the shape of a funnel or cone. A measure of the expansion can be a conical angle of approximately 4°, to cite just one example. The conical angle can range from 1° to 45°. In some preferred embodiments, rather smaller conical angles may be preferred.

In some preferred embodiments, the portion 6 opens into the portion 7 when the needle support 1 is connected to the continuation 2. The portions 6 and 7 can respectively exhibit an identical fluid-guiding cross-section, e.g. an identical inner diameter, at the aperture.

The portion 6 can exhibit a cross-sectional ratio of its maximum fluid-guiding cross-section to its minimum fluid-guiding cross-section of 4:1. Cross-sectional ratios of 2:1 to 10:1 have proven to be advantageous. The ratio can also be 2.5:1 or other suitable ratio.

The fluid to be administered is supplied from the environment of the continuation 2 to the fluid channel via an opening 4. Although one opening 4 would in principle be sufficient, two openings 4 are shown in the depicted example, which are arranged opposite each other and on the side of the fluid channel 6. A part of the fluid channel 6 is thus arranged between the openings 4. The openings 4 have the shape of an elongated hole which can be between 1 and 4 mm long, e.g. 3 mm, and can exhibit a width of the diameter of the part of the fluid channel 6 which is arranged between the openings. The overall cross-sectional area of the openings 4, or one of them, can be larger than the minimum fluid-guiding cross-section of the portion 6. The ratio of the overall cross-sectional area of the openings 4 and the minimum fluid-guiding cross-section of the portion 6 can be 7:1. The overall cross-sectional area of the openings 4 should be at least as large as the minimum fluid-guiding cross-section. The cross-sectional ratio can range from 2:1 to 10:1 and to other suitable ratios.

The continuation 2 comprises a rotationally symmetrical tip which is embodied in this example as a cone and forms the distal end of the continuation 2. The arrangement of the two openings 4 causes the fluid to be supplied laterally, i.e. transverse to the longitudinal axis, and subsequently transported in the fluid-guiding channel (which may be thought of as comprising elements or portions 6, 7, 8, 10) along the longitudinal axis in the direction of the needle 3.

The continuation 2 comprises a connecting portion 12 using which the unit consisting of the needle support 1, the continuation 2 and the needle 3 can be connected, indirectly or directly as applicable, to a part of the injection device. Alternatively, the needle support 1 could comprise the portion 12.

In the region of the fluid channel portion 7, the proximal end of the needle support 1 comprises a recess which is surrounded by an annular protrusion. In this example, the annular protrusion is concentric with the longitudinal axis of the needle unit 100. The distal end of the continuation 2 exhibits a shape which approximately corresponds to a negative mold of the proximal facing side of the needle support 1. The distal facing side of the continuation 2 comprises an annular groove into which the annular protrusion is arranged when the continuation 2 is joined together with the needle support 1, and comprises a truncated conical protrusion which engages with the recess of the needle support 1 when the continuation 2 and the needle support 1 are joined together. This achieves join or connection 9 which is fluid-proof The mutual engagement of the two facing sides increases the surface which can be used for a connection 9.

The injection needle 3 can be selected from needles having a wide range of diameters, wall thicknesses and lengths; for example, it is equally possible to provide a 23 gauge needle or a 31 gauge needle. The injectable length of the injection needle 3 can be selected for a subcutaneous or transcutaneous injection.

Figure 1:
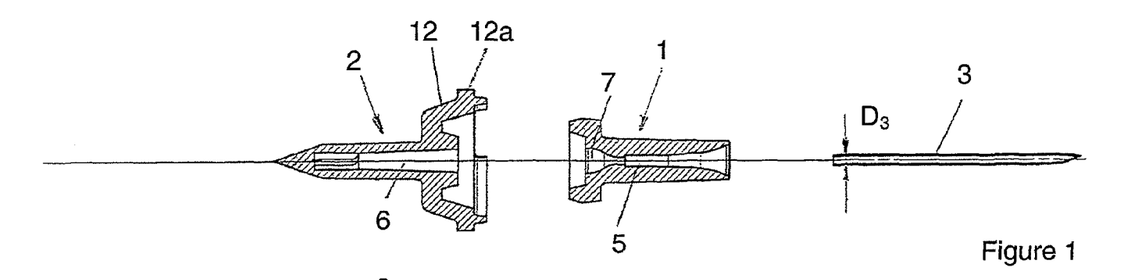
FIGS. 1 to 4 show parts of one embodiment of a needle unit in accordance with the present invention.
Figure 2:
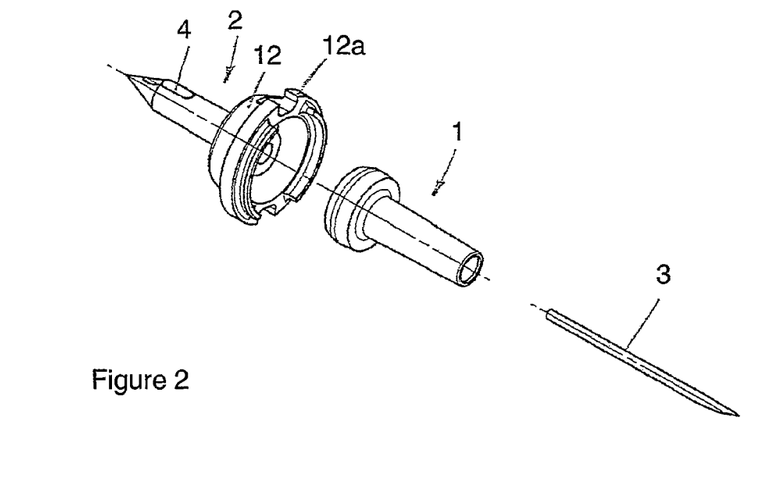
Figure 3:
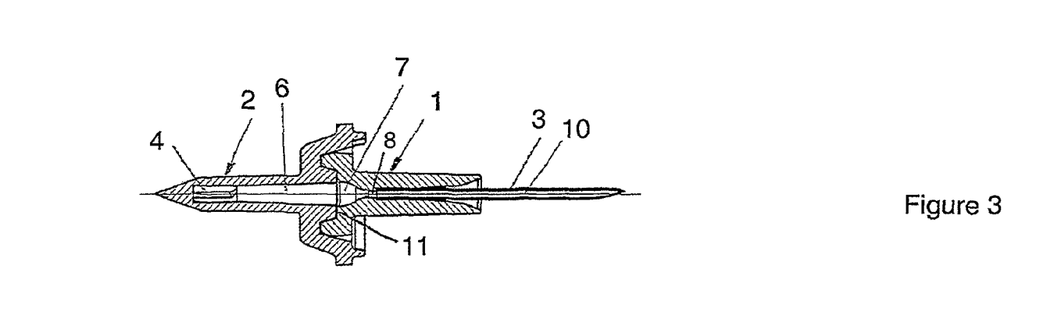
Figure 4:
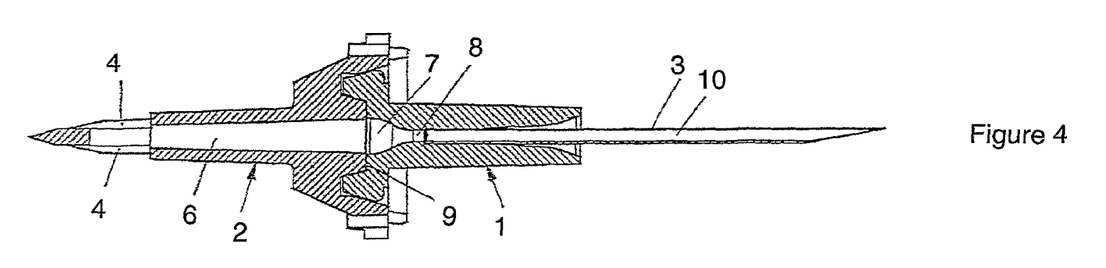
Figures 5, 6:
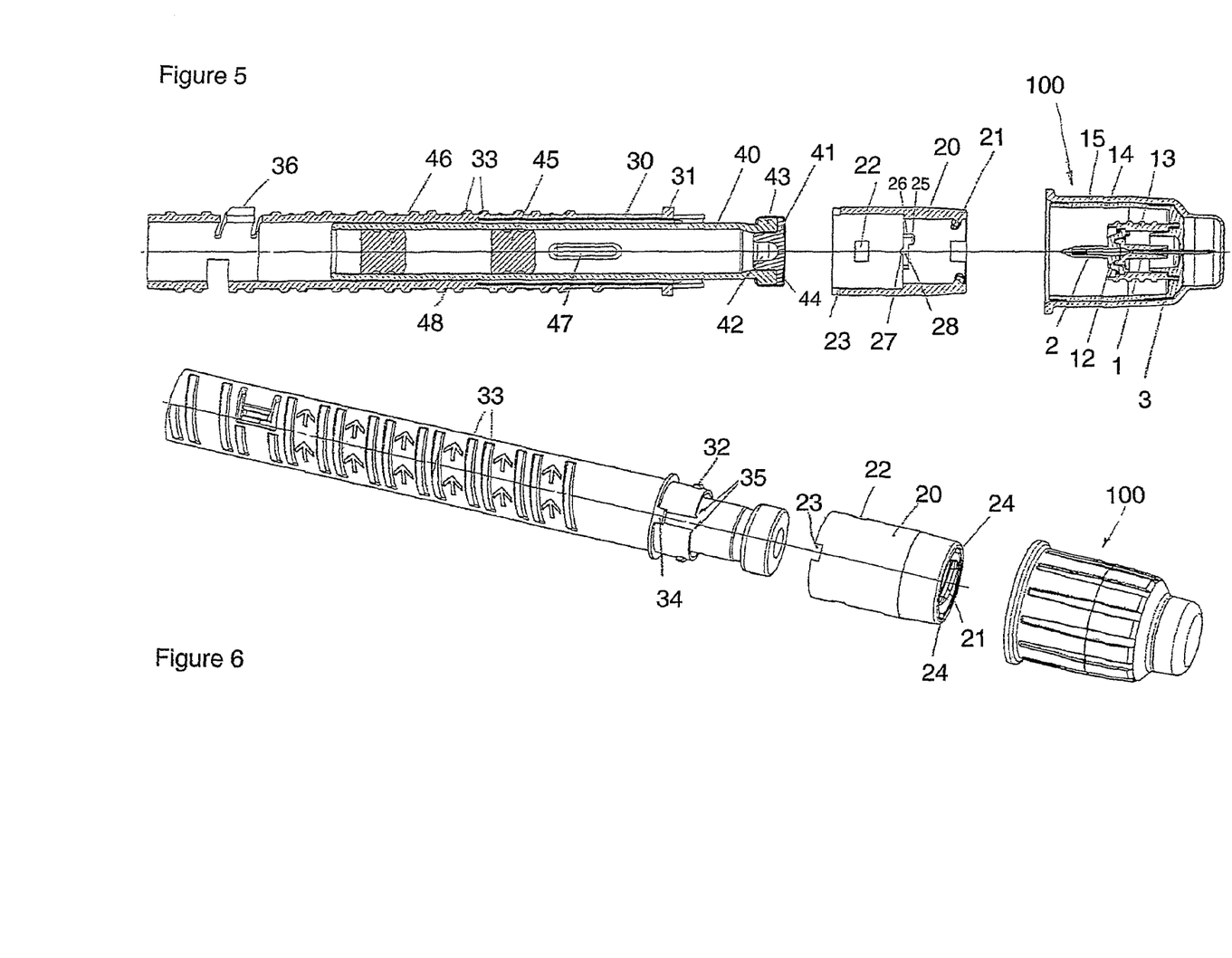
FIGS. 5 and 6 show the individual parts of an embodiment of an ampoule holder and a preferred embodiment of a needle unit in accordance with the present invention.

One embodiment of a complete needle unit 100 in accordance with the present invention is shown in FIGS. 5 and 6. The unit, comprising the needle support 1, the continuation 2 and the injection needle 3, is connected to a fastening portion 13 via the connecting portion 12. The sleeve-shaped fastening portion 13 serves to be connected to a fastener or fastening member 20 and comprises a thread, e.g. an outer thread, for this purpose. The unit forming the fluid channel (which, again, may be thought of and/or referred to as comprising elements, parts or portions 6, 7, 8, 10) is connected, axially fixed, to the fastening portion 13. Depending on its application, the unit 100 can be rotatable or non-rotatable relative to the fastening portion 13. The unit further comprises a connecting protrusion 12a which engages with an annular groove 13c formed on the inner circumference of the fastening portion 13. The fastening portion 13 is connected such that it is rotationally and axially fixed to a casing 14. The fastening portion 13 and the casing 14 could in principle also be formed integrally, however forming them in a number of parts has advantages when manufacturing the needle unit 100. The sleeve-shaped casing 14 surrounds both the fastening portion 13 and the continuation 2 and its tip on the circumferential side. The casing 14 extends in the proximal direction, at least as far as the tip or—as shown here—beyond the tip, such that the tip of the continuation 2 does not protrude beyond the proximal end of the casing 14. The risk of unintentional piercing by the tip of the continuation 2 is reduced by the casing 14 protruding beyond the tip 2. An annular gap is formed between the fastening portion 13 and the casing 14. The casing 14, the fastening portion 13 and the unit 100 are arranged concentrically with respect to each other.

The distal end of the casing 14 comprises a facing area comprising an opening through which the injection needle 3 protrudes by a length. This length substantially corresponds to the injection depth of the injection needle 3, since the distal end of the casing forms an abutment area for the patient's body. For reasons of space, the casing 14 can comprise a cavity for the needle support 1.

The needle unit 100 also comprises a packaging sleeve 15 which in the position shown in FIGS. 5 and 6 is arranged concentrically over the outer circumference of the casing 14. The packaging sleeve 15 is held by the casing 14, e.g. in a frictional fit. The packaging sleeve 15 surrounds the casing 14 completely over its circumference and also over its length. In some preferred embodiments, the packaging sleeve 15 proximally protrudes at least slightly beyond the proximal end of the casing 14. The opening which is formed at the proximal end of the packaging sleeve 15, through which the casing 14 together with the unit 100 can be inserted or removed, can be sealed with a so-called peel or release film in the delivered state of the needle unit 100, to keep the contents of the packaging sleeve 15 sterile or at least to protect them from contamination. The packaging sleeve 15 distally protrudes beyond the distal end of the needle 3, where it is sealed on its facing side. In this respect, the packaging sleeve 15 forms a closed cup which comprises an opening at its proximal end. The outer circumference of the packaging sleeve 15 comprises a structure which better enables a user of the device to apply a torque to the packaging sleeve 15, about the longitudinal axis. Since, when completely placed on the casing 14, the packaging sleeve 15 is connected, such that it is rotationally fixed, to the casing 14 at least in a frictional fit, and alternatively or additionally in a positive fit, the casing 14 together with the fastening portion 13 is rotated along with the packaging sleeve 15 when a torque is applied to the packaging sleeve 15.

Figure 10:
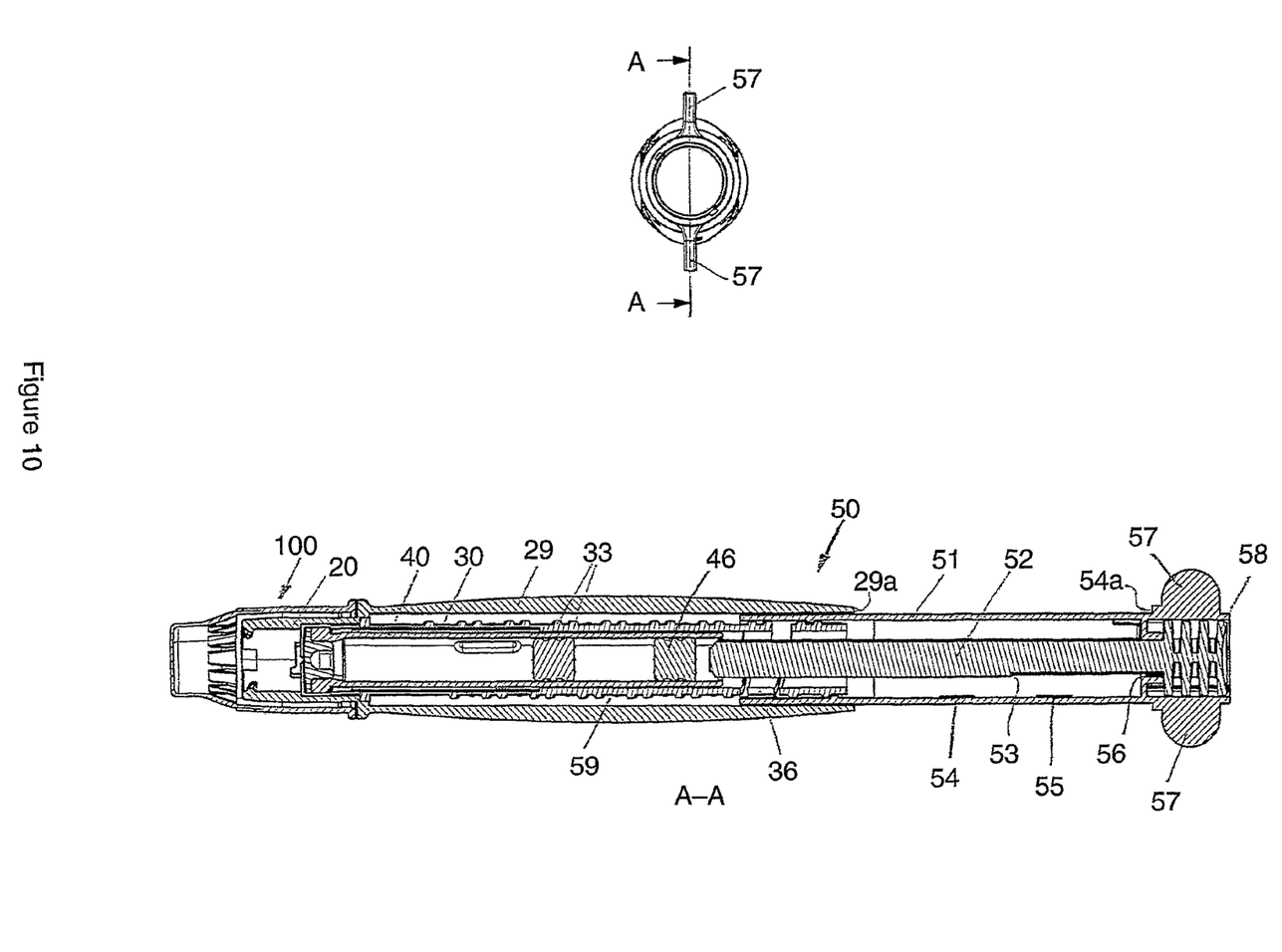
FIG. 10 depicts a preferred embodiment of an administering device in accordance with the present invention.

The needle unit 100 can be attached to an injection device 50 (FIG. 10). Parts of the injection device, namely an ampoule receptacle 30 and a fastening member 20, are shown separately together with an ampoule 40 in FIGS. 5 and 6, assembled in FIG. 7 and assembled with a needle unit 100 attached in FIG. 8.

The ampoule 40, such as is shown for example in FIGS. 5 and 6, is a two-chamber ampoule (which may also be referred to as a two-chamber carpoule), one characteristic of which is that a product to be administered is merged or mixed, directly before being administered, from two components which for storage are contained in two different chambers. The distal chamber, i.e. the chamber which is arranged between a seal (comprised of parts 41, 42, 43, 44) and a first plunger 45, can, for example, be partially or completely filled with a solid such as a granular or powdery material. A second chamber is situated proximally with respect to the first plunger 45 and is arranged between the first plunger 45 and a second plunger 46. A fluid constituent of the drug can be situated in this chamber. Both plungers 45, 46 abut a hollow-cylindrical casing portion 48 of the ampoule 40, forming a seal, and can be shifted along the casing portion 48.

In the region of the casing portion, the ampoule 40 comprises a bypass 47 which forms a camber outwardly. The bypass 47 is axially longer than the first plunger 45.

For mixing, a pressure is exerted in the distal direction on the second plunger 46 and transferred onto the first plunger 45 via the fluid product in the chamber between the plunger 45 and the plunger 46. When the second plunger 46 is shifted in the distal direction, the first plunger 45 is thus also shifted, as far as the region of the bypass 47. Due to the camber of the bypass 47, it is possible—providing the plunger 45 is situated completely in the region of the bypass 47—for the fluid product to flow past the plunger 45 and into the distal chamber and to mix with the product constituent situated therein. The user can assist mixing by shaking the device. The fluid product has been completely removed from the proximal chamber when the second plunger 46 abuts against the first plunger 45. The mixture consisting of the two product constituents can form a homogeneous or a heterogeneous mixture. The heterogeneous mixture of a fluid constituent with particles of solid is generally referred to as a dispersion, specifically a suspension. The product to be administered can then be delivered via the fluid channel of the needle unit 100, the openings 4 of which are situated within the ampoule, in the region 42, by shifting the plungers 45 and 46 in the distal direction along the hollow-cylindrical casing portion 48.

The ampoule 40 comprises a seal (which, again, may be thought of and/or referred to as being comprised of elements 41, 42, 43, 44) which comprises a septum 41 which can be penetrated by the continuation 2. Such septa can be made of rubber or natural rubber or another suitable material.

The septum 41 comprises a disc-shaped portion and a hollow-cylindrical portion connected to it in the proximal direction. The hollow-cylindrical portion forms a cavity in its interior, in which the openings 4 of the completely attached needle unit 100 are positioned in some preferred embodiments. The outer side of the hollow-cylindrical portion of the septum 41 centers the septum 41 on the inner circumference of the ampoule 40, e.g. at the distal end of the ampoule 40. An annularly circumferential bulge is formed at the distal end of the ampoule 40 and protrudes radially outwardly and may be referred to generally as a projection. The bulge 43 protrudes radially beyond the outer circumference of the hollow-cylindrical portion 48 of the ampoule 40. In other words, the ampoule 40 exhibits a larger outer diameter at the point of the bulge 43 than in the region of the hollow-cylindrical portion 48. In this example, the outer diameter of the bulge 43 also forms the maximum outer diameter of the ampoule 40. The bulge 43 is integrally connected to the hollow-cylindrical portion 48. This part of the ampoule can be formed from plastic or glass. The disc-shaped part of the septum 41 exhibits approximately the same outer diameter as the bulge 43. The septum 41 and the bulge 43 are held together by a remolded or deformable part 44 which can be produced from a metal sheet. This part may also be referred to as a cap. The remolded part 44 clasps the septum 41 and the bulge 43 over their circumference and both distally with respect to the septum 41 and proximally with respect to the bulge 43. The remolded part 44 connects the bulge 43 and the septum 41 such that they are axially fixed, i.e. holds them together in a fluid seal. The distal facing side of the remolded part 44 comprises an opening which can be circular and through which the continuation 2 can be inserted through the septum 41 into the interior of the ampoule 40 which has already been mixed.

Between the hollow-cylindrical part 48 and the bulge 43, the ampoule 40 comprises a neck which is constricted relative to the outer diameter of the portion 48, such that the remolded part 44 can be reformed or deformed more completely, e.g. further inwardly, around the proximal end of the bulge 43. The proximal end of the ampoule 40 is open, such that a plunger rod 52 (FIG. 10) can be slid into the ampoule 40 and onto the second plunger 46.

The fastener or fastening member 20 can be fastened to or carried by the ampoule receptacle 30. The fastening member 20 and the ampoule receptacle 30 may be thought of and/or referred to as the ampoule holder. The fastening member 20 is sleeve-shaped and connected, e.g. latched, to the ampoule receptacle 30 such that it is rotationally and axially fixed. The rotational fixation is achieved by the engagement between the cavity 23 and the cam 34. The axially fixed arrangement of the fastening member 20 on the ampoule receptacle 30 is achieved by the cam 32 latching into the windows 22.

As can be seen from FIGS. 5 and 6, the ampoule 40 is inserted into the ampoule receptacle 30 via a distal opening of the sleeve-shaped ampoule receptacle 30. The outer diameter of the seal is larger than the inner diameter of the ampoule receptacle 30, such that the seal abuts the distal end of the ampoule receptacle 30. As can be seen from FIG. 7, the seal of the ampoule 40 is axially enclosed between the ampoule receptacle 30 and the fastening member 20 and thus axially fixed. The enclosure can allow the ampoule 40 a small axial clearance. However, the enclosure may be such that the axial clearance is further reduced. To this end, the distal end of the ampoule receptacle 30 comprises at least one projection—in this case, four projections 35—which extend in the distal direction and which the seal abuts. The at least one projection 35 can be arranged on the ampoule holder, e.g. on the ampoule receptacle, rigidly as shown here or such that it is loaded or biased. Arranging it loaded has the additional advantage that an axial clearance is virtually no longer present. The loading arrangement can be achieved by providing a slit, which extends in the circumferential direction, proximally with respect to the at least one projection 35, such that the stay which is situated between the slit and the projection 35 can be sprung in the axial direction.

Figure 7:
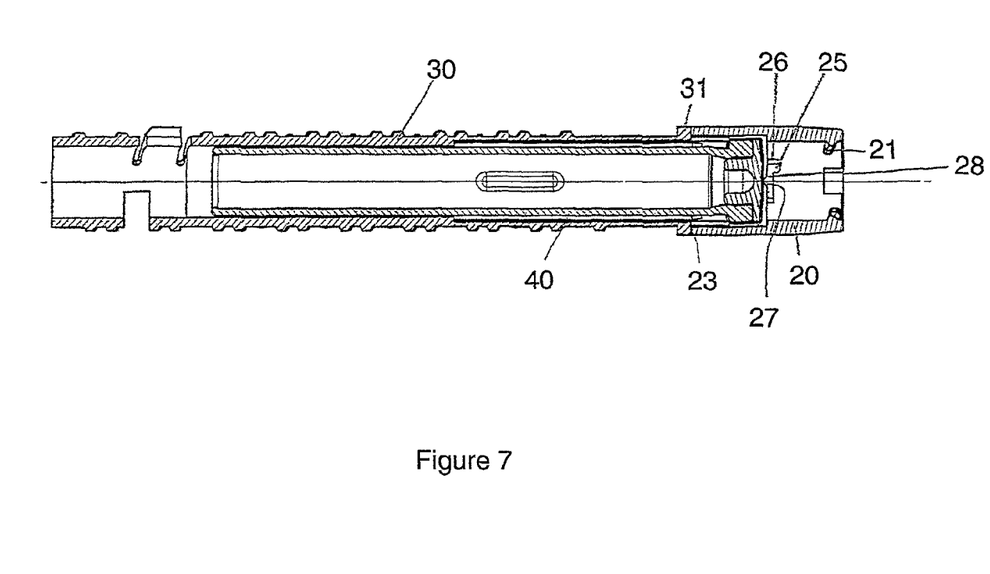
FIG. 7 depicts an assembled ampoule holder, together with an ampoule accommodated in it.

The seal can be enclosed from the distal side by a collar formed on the inner circumference of the fastening member 20. The collar can partially or completely encircle the circumference. A projection 28 which extends inwardly from the inner circumferential area is provided, either as an alternative to or in addition to the collar, and can serve as an enclosure for the seal. On its side pointing toward the seal, the projection 28 comprises a projection, e.g. a cam 27, which presses against the distal facing area of the seal, against the remolded part 44. A part of the seal, such as the remolded part 44, can be elastically or plastically deformed by the point-focussed burden of the cam 27, thus achieving a secure, low-clearance enclosure of the seal between the ampoule receptacle 30 and the fastening member 20. The cam 27 can be arranged rigidly or such that it is urged in the longitudinal direction.

As can be seen from FIGS. 5 to 7, the outer circumference of the ampoule receptacle 30 comprises an outer thread 33 via which the ampoule holder can be screwed into a casing 51 of the injection device 50 (FIG. 10), wherein the casing 51 comprises a corresponding inner thread for the outer thread 33 of the ampoule holder. To make the intuitive handling of the device 50 easier for the user, at least one arrow can be arranged on the ampoule holder, e.g. on the circumference of the ampoule receptacle 30, which points in the direction of rotation for mixing. In some preferred embodiments, a multitude of arrows are distributed over the length of the ampoule receptacle 30. The arrows can be printed on or formed as elevations or recesses which are molded as the ampoule receptacle 30 is injection-molded. The at least one arrow can be arranged between adjacent flights of the thread 33.

The ampoule holder, e.g. the ampoule receptacle 30, also comprises a latching member 36 which is mounted such that it is biased in the radial direction. The springiness or resiliency is generated by an arm which extends in the circumferential direction and which is formed on the ampoule receptacle 30 and on which the latching member or cam 36 is formed. The function of said latching member 36 is described below with reference to FIG. 10.

The fastening member 20 also comprises a single-flight or multiple-flight thread—in this example, in the form of two threaded portions 21 which enable the needle unit 100, comprising the outer thread situated on the fastening portion 13, to be screwed onto the injection device. Due to the axial movement of the continuation 2 when the needle unit 100 is screwed on, the tip of the continuation 2 penetrates the septum 41. The torque required for screwing on the needle unit 100 is applied via the packaging sleeve 15 or the casing 14. Once the needle unit 100 has been completely screwed on, it assumes the position shown in FIG. 8. The openings in this case are then situated within the ampoule 40, such that the distal end of the injection needle 3 is fluidically connected to the interior of the ampoule 40. A distal portion of the fastening member 20 is then situated in the annular gap between the fastening portion 13 and the casing 14.

Figure 8:
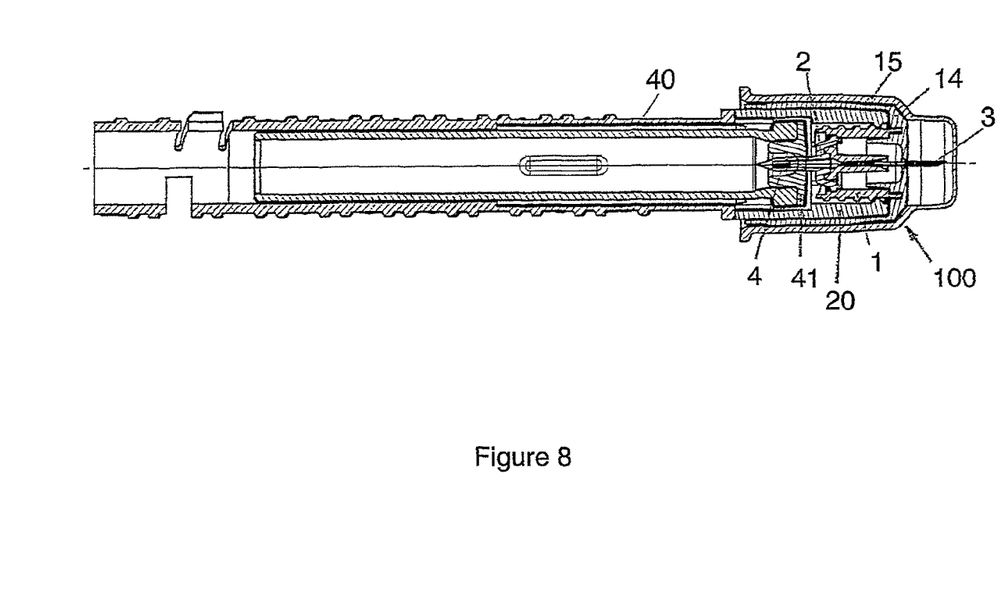
FIG. 8 shows the ampoule holder of FIG. 7, with a needle unit arranged on it and on the ampoule.

Providing the unit 100 is arranged such that it can be rotated relative to the fastening portion 13, it is possible for the continuation to inject into or pierce the septum 41 with a purely axial movement. This can offer advantages with regard to the seal between the septum and the continuation. If the unit is arranged such that it is rotationally fixed relative to the fastening portion 13, the septum is penetrated by the continuation 2 by a combined rotational and axial movement, which offers advantages with regard to the torque required for screwing on the needle unit 100.

Figure 9:
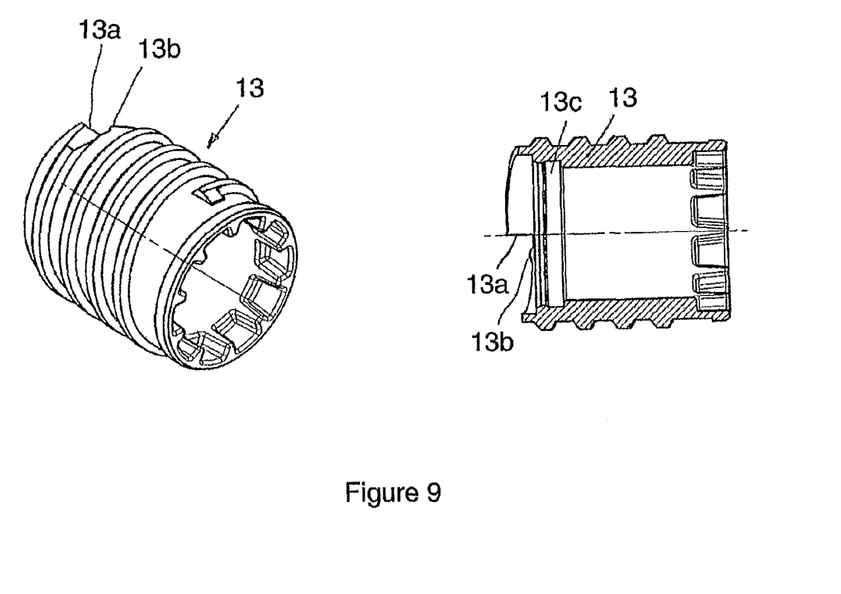
FIG. 9 depicts a preferred embodiment of a fastening portion of a needle unit in accordance with the present invention.

As can be seen from FIGS. 5 and 9, the fastening member 20 comprises an abutment 26 which acts in the circumferential direction, and the fastening portion 13 comprises an abutment 13a which likewise acts in the circumferential direction. A number of such abutments—such as two such abutments in this example—can also be arranged on each of the fastening member 20 and the fastening portion 13.

The abutments 26 and 13a form an abutting pair and are positioned such that they pass into a rotational abutment when the needle unit 100 is in its completely screwed-on position (FIG. 8), thus securely preventing any further rotation. The abutment 13a is formed on the proximal end of the fastening portion 13. The abutment 26 is formed on the projection 28 of the fastening member 20. An axial abutment could also optionally be provided instead of a rotational abutment, however the rotational abutment has the advantage over an axial abutment that the parts which pass into abutment are not burdened as much, since due to the translation generated by the thread pitch, a significantly greater force can be achieved by a particular torque in the axial direction than in the circumferential direction.

The fastening member 20 can comprise one or more projections 24 or 25 which latch to the needle unit 100 shortly before the rotational abutment is reached, such that a reverse rotation of the needle unit 100 in the opposite direction is only possible using an increased torque or is not at all possible, i.e. is only possible by destroying a component or a part of a component. Alternatively, cavities which serve the same purpose can be provided instead of the projections 24, 25. Due to the latching when the needle unit 100 is screwed on, the user obtains on the one hand a tactile signal which indicates to him/her that the needle unit 100 has then been completely screwed on. On the other hand, it prevents an unintentional reverse rotation, such that the risk of misapplication can be reduced. Where cavities or cams 24 are provided as the reverse rotation block, these engage with the casing 14 of the needle unit 100, with its facing side formed in the annular gap. For this purpose, the facing side can comprise at least one projection—such as for example ribs or a cam—or a cavity, which is traversed shortly before or when the rotational abutment is reached.

A projection 25 can alternatively or additionally be provided in the form of a cam which protrudes in the distal direction and traverses a projection 13b, e.g. a cam, shortly before or when the rotational abutment is reached. The projection 13b is arranged on the proximal facing side of the fastening portion 13 and, offset in the circumferential direction, in front of the abutment 13a. The distance between the projection 13b and the abutment 13a can correspond approximately to the width of the projection 25 as measured in the circumferential direction, which means that the cam 25 is held between the abutment 13a and the projection 13b when the needle unit 100 is completely screwed on.

A projection 13b which allows a screwing movement counter to the screwing-on direction can comprise flanks which are flattened on both sides in the circumferential direction. A projection 13b which is intended to prevent a rotation counter to the screwing-on direction from being possible can exhibit the shape of a serrated tooth which allows the projection 13b to be traversed but prevents a reverse rotation due to the steep area of the serrated tooth. The same applies of course to the latching between the cavities or projections 24 and the cavities or projections on the casing 14.

The projection 13b is arranged on the facing side of the fastening portion which is embodied as a helical rail. The helical shape exhibits approximately the pitch of the thread of the fastening portion 13.

A preferred embodiment of an injection device in accordance with the present invention is shown in FIG. 10. The device is a mixing and delivering device 50 which for the sake of simplicity is referred to in the following as an injection device. The injection device 50 comprises a casing 51 comprising an inner thread into which the ampoule holder shown in FIG. 7, which comprises an outer thread 33, can be screwed. A plunger rod 52 is arranged within the sleeve-shaped casing 51 and is connected to an injection button 58. When the injection device 50 is in its initial state, i.e. before the product constituents of the two-chamber ampoule 40 have been mixed, the injection button 58 is surrounded over its axial length, e.g. completely, by the casing 51. Two wings 57 which point radially outwardly are arranged on the casing 51. The small plate-shaped wings make it easier for the user to hold the device and apply a necessary torque when mixing. The wings 57 thus serve as a gripping aid and, in combination with a gripping portion 29, improve the intuitively correct handling. The wings 57 are situated at the proximal (rear) end of the device 50.

In one preferred embodiment, the injection device comprises an outer sleeve 29 which serves as a gripping portion and which the user of the device 50 can clasp in one hand, while he or she screws the casing 51 onto the ampoule holder, into the annular gap formed between the outer sleeve 29 and the ampoule receptacle 30, with the other hand at the wings 57. This has the advantage that it allows patients who have restricted motor abilities to securely mix the product constituents. At the end of the mixing sequence and as applicable a priming sequence, the abutment 29a formed at the proximal end of the outer sleeve 29 and the abutment 54a formed by the casing 51 in the region of the distal end pass into a rotational or axial abutment, such that this indicates to the user that the mixing process and priming process are complete.

In an alternative, also preferred embodiment, the injection device 50 is without the outer sleeve 29. The user of the injection device can clasp the packaging sleeve 15 or the casing 14 with one hand and the casing 51 or as applicable wings 57 fastened to it with the other hand, to apply the torque. Mixing is analogous relative to the embodiment comprising a sleeve-shaped gripping portion 29, wherein the end of the mixing process is indicated by the rotational or axial abutment of the distal end of the casing 51 against the annularly circumferential collar of the ampoule holder which is indicated in FIG. 5 by the reference sign 31. This variant is also possible in the embodiment comprising an outer sleeve 29. Due to the rotational abutments 26, 13a between the needle unit 100 and the ampoule holder, it is possible to securely prevent the components involved in the abutment from being overloaded, even when the torque for mixing passes via the needle unit 100.

In both exemplary embodiments of an injection device 50, it is the case that when the ampoule receptacle 30 and the casing 51 are screwed into each other when mixing the product constituents, the plunger rod 52 passes into abutment with the plunger 46, thus moving the casing 51 in the distal direction relative to the plunger rod 52, wherein the plunger rod 52 remains axially fixed relative to the ampoule 40 due to the static friction between the plunger/plungers 45, 46 and the ampoule wall. The plunger rod 52 comprises a cavity, on the distal end 53 of which an abutment 53 is formed. While the ampoule receptacle 30 is being screwed into the casing 51, the axial abutment 56 which is formed by the casing 51 is moved in the direction of the abutment 53. The injection button 58 protrudes proximally out of the casing 51 during this movement. As soon as the abutment 56 abuts against the abutment 53, the plunger rod 52 is slaved such that the plunger rod 52 participates in the axial movement of the casing 51 in the distal direction relative to the ampoule receptacle 30 and relative to the ampoule 40. The plunger rod 52 can then shift the plunger 46 in the distal direction, thus performing the mixing sequence such as has been described further above. At the end of mixing, the latching member 36 can engage with or traverse a latching element 54, which can indicate the end of the mixing process to the user. The user then shakes the device 50, such that the product constituents are mixed. The user can subsequently prime the device to remove from the ampoule 40 any air which may still be contained in the ampoule 40. For this purpose, the user can continue the screwing movement of the casing 51 relative to the ampoule receptacle 30, wherein both plungers are then shifted and the volume in the product container is reduced, thus expelling the air from the product container 40 via the fluid channel of the needle unit 100. At the end of the priming sequence, the latching member 36 can latch into another latching element 55, likewise formed on the inner circumference of the casing 51, thus indicating the end of the priming sequence to the user. The device 50 is then ready for a product delivery which, after the needle 3 has been injected into a desired point on the body, is initiated by pressing the injection button 58 in the distal direction relative to the casing 51 and relative to the ampoule 40.

The latching elements 54 and 55 can be formed such that an acoustic or tactile signal is generated during an interaction, e.g. when the latching member 36 traverses the latching elements 54 and 55. By forming the flanks on the latching member 36 to be asymmetrical in the circumferential direction, it is also possible that once the latching member 36 has reached the latching elements 54 or 55, any further rotation in a direction counter to the mixing or priming movement is no longer possible.

In the embodiment comprising an outer sleeve 29, the latter can be connected to the ampoule receptacle 30 such that it is rotationally and axially fixed, for example by a latching connection or by forming it integrally with the ampoule receptacle 30 or the fastening member 20. The outer sleeve 29 can extend from the fastening member 20 far enough in the proximal direction that its proximal end proximally protrudes beyond the proximal end of the ampoule 40 and also beyond the proximal end of the product container receptacle 30.

The embodiment shown in FIG. 10 has the advantage that the user of the device 50 does not see any thread, which may be advantageous in the case of people who regard technology with skepticism. A color coding may be given on the outer side of the casing 51, from which it is additionally possible to optically tell whether the device is being mixed or primed or whether the device is ready for a product delivery. A first color can be arranged such that it is covered by the first sleeve 29 after mixing is complete. A second, different color can also be provided which disappears beneath the second sleeve 29 after priming. A third color can then be provided which indicates to the user that the device is then ready for a product delivery. To improve the grip, the outer sleeve 29 can be provided with a friction-increasing structure, for example texture, ribs or dimples, or a friction-increasing material such as a rubber layer. The same also applies to the wings 57.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An ampoule and an ampoule holder, the ampoule comprising a cylindrical casing portion with an outer diameter, wherein the cylindrical casing holds a moveable plunger; and a seal which seals a facing side of the casing portion, wherein the seal protrudes radially beyond the outer diameter and comprises a projection formed at a distal end of the casing portion wherein the projection is connected integrally to the casing and the seal is adapted to abut and extend from a distal end opening of the ampoule holder, the ampoule holder having an inner dimension large enough to receive the ampoule except for the seal projection formed at the distal end of the ampoule.

2. The ampoule according to claim 1, wherein the ampoule is a two-chamber ampoule.

3. The ampoule according to claim 2, wherein the seal can be penetrated by a piercing object with a fluid channel with a fluid-guiding cross-section that is larger than the fluid-guiding cross-section of a delivery needle in fluid communication with the piercing object.

4. The ampoule according to claim 3, wherein the seal comprises a septum enclosed by an annular metal part at least in the region of the radial protrusion.

5. An ampoule and an ampoule holder, the ampoule comprising a casing, a facing side and a seal, wherein the casing has an outer diameter and the seal extends radially beyond the outer diameter and seals the facing side, and the ampoule holder comprising an ampoule receptacle with an inner diameter and a fastening member, wherein the radial extension of the seal has a diameter exceeding the inner diameter of the receptacle and is between the ampoule receptacle and the fastening member wherein the radial extension is connected integrally to the casing and the fastening member affixes a proximal side of the radial extension of the seal abutting the distal end of the ampoule receptacle, upon the ampoule being inserted in the ampoule holder.

6. The ampoule and ampoule holder according to claim 5, wherein the ampoule is inserted into the ampoule receptacle at its distal opening with the facing side extending away from the distal end of the ampoule holder.

7. The ampoule and ampoule holder according to claim 5, wherein at least one of the ampoule receptacle and the fastening member comprises at least one projection directed toward the seal.

8. The ampoule and ampoule holder according to claim 7, wherein the at least one projection is on the facing side or on a radial projection of the fastening member.

9. The ampoule and ampoule holder according to claim 5, wherein a needle unit is fastened to the ampoule holder.

10. The ampoule and ampoule holder according to claim 5, wherein the fastening member is at least one of axially and rotationally fixed to the ampoule receptacle.

11. The ampoule and ampoule holder according to claim 5, wherein the ampoule is a two-chamber ampoule and comprises a recess for forming a bypass for the two-chamber ampoule.

12. The ampoule and ampoule holder according to claim 5, wherein the ampoule receptacle comprises a fastener via which the ampoule holder can be fastened to an injection device and, when fastened, moved into the injection device by a combined axial and rotational movement.

* * * * *